United States Patent [19]

Kanazawa

[11] 4,418,689
[45] Dec. 6, 1983

[54] LASER DEVICE FOR AN ENDOSCOPE

[75] Inventor: Akira Kanazawa, Hachioji, Japan

[73] Assignee: Olympus Optical Co., Ltd., Tokyo, Japan

[21] Appl. No.: 302,468

[22] Filed: Sep. 15, 1981

[30] Foreign Application Priority Data

Sep. 22, 1980 [JP] Japan ................................ 55-132196
Oct. 24, 1980 [JP] Japan ............................ 55-151734[U]

[51] Int. Cl.³ .............................................. A61B 1/06
[52] U.S. Cl. .................................................... 128/6
[58] Field of Search ........................................ 128/4–6,
128/303.1, 303.11, 303.12, 395; 372/4; 350/315

[56] References Cited

U.S. PATENT DOCUMENTS

| | | | |
|---|---|---|---|
| 1,613,562 | 1/1927 | Frost | 350/315 |
| 3,642,007 | 2/1972 | Roberts et al. | 128/303.1 |
| 3,659,613 | 5/1972 | Bredemeier | 128/395 |
| 3,710,798 | 1/1973 | Bredemeier | 128/303.1 |
| 3,769,963 | 11/1973 | Goldman et al. | 128/303.1 |
| 3,865,114 | 2/1975 | Sharon | 128/303.1 |
| 4,043,646 | 8/1977 | Heine et al. | 350/315 |
| 4,249,533 | 2/1981 | Kaniya | 128/303.1 |

FOREIGN PATENT DOCUMENTS 2809007 9/1979 Fed. Rep. of Germany ... 128/303.1

*Primary Examiner*—Kyle L. Howell
*Assistant Examiner*—Max F. Hindenburg

[57] ABSTRACT

A laser device for an endoscope capable of ejecting medical treatment laser beams and illumination light beams into the endoscope through a laser beam probe comprises a medical treatment laser beam oscillator which is received in a housing to emit laser beams, an illumination light source which is received in the housing and includes a turntable with a plurality of different color filters to selectively emit at least two visible rays having different colors, and an optical system which brings the optical axis of laser beams emitted from the oscillator in alignment with the optical axis of visible rays issued from the illumination light source, thereby conducting said laser beams and illumination light beams to a light-emitting section of the housing.

3 Claims, 6 Drawing Figures

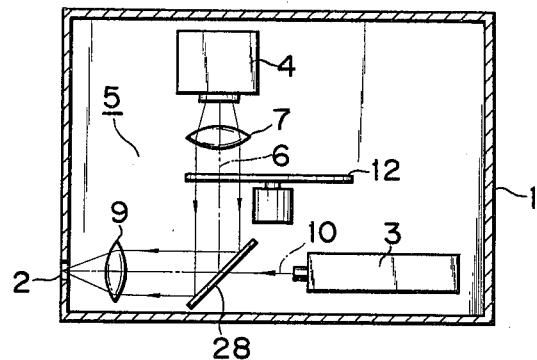
FIG. 4
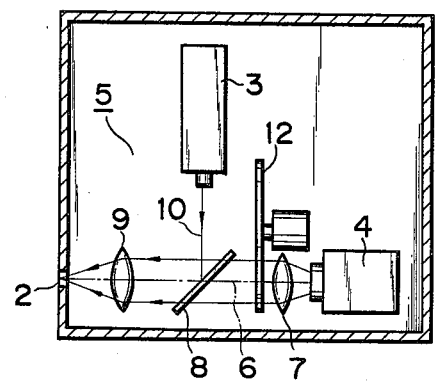
FIG. 5
FIG. 6
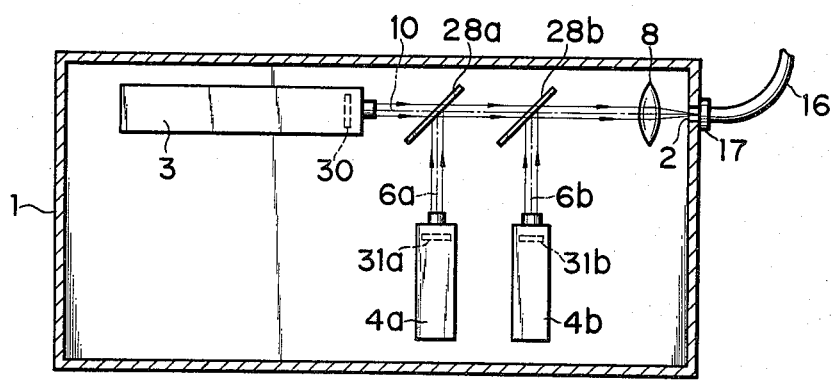

LASER DEVICE FOR AN ENDOSCOPE

BACKGROUND OF THE INVENTION

This invention relates to a laser device for an endoscope, wherein a light-transmitter is set in the insertion section of an endoscope, a laser beam and guide beam are sent forth by means of the light-transmitter, and a patient's affected spot is medically treated by the laser beam thus guided.

The insertion section of an endoscope generally holds a light-guiding path such as an optical fiber bundle and an image-transmitting path such as an image guide fiber bundle.

Guide light beams transmitted through a light guide fiber bundle, for example, helium-neon laser beam and light beam issued from a xenon lamp are ejected outward from the distal end of an endoscope. An image of an object of observation, for example, a patient's inner coeliac wall illuminated by such guide beams is transmitted through the image guide to the observation section of the endoscope at the proximal end. The coeliac wall is observed through an eyepiece lens system of the observation section. A laser beam transmitter (laser probe) is received in the insertion channel of the endoscope. A medical treatment laser beam supplied from an external infrared laser beam oscillator is ejected from the end portion of the light transmitter for the excision of a patient's coeliac affected spot.

It is known that when rendered morbid, part of an inner coeliac wall presents a different color from the wholesome portions of said coeliac wall. Since, however, a guide light is generally formed of a white ray, a small affected portion of the inner coeliac wall is difficult to be distinguished from the wholesome portions thereof. Therefore, such small affected portion has hitherto beam likely to be overlooked.

The medical treatment laser beam is a colorless ray (infrared ray) or an extremely faint visible ray. Therefore, it is extremely difficult to observe those portions of the coeliac wall which are illuminated by such laser ray in the observation section of the endoscope. The aforesaid guide light beam is used to illuminate a relatively large area of an object of observation independently of a laser beam emitting section. Therefore, difficulties have been experienced in accurately directing laser beams to a patient's affected coeliac spot while looking at the object of observation in the endoscope observation section. Actually therefore, the endoscope operator tries to set a patient's affected coeliac spot in that portion of the view field of the endoscope observation section which is supposedly illuminated by laser beams.

SUMMARY OF THE INVENTION

It is accordingly the object of this invention to provide a laser device for an endoscope which makes it easy to search for a patient's affected coeliac spot by an endoscope and assures the medical treatment of said affected spot by laser beams while guide beams are projected thereon.

BRIEF DESCRIPTION OF THE DRAWINGS

FIGS. 2 to 6 are schematic sectional views of endoscope laser devices according to other embodiments of the invention.

DETAILED DESCRIPTION OF THE PREFERRED EMBODIMENTS

Figure 1:
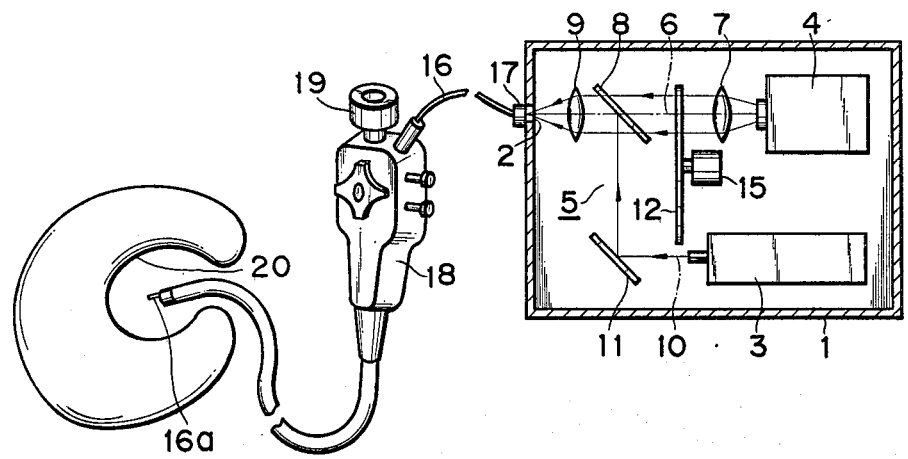
FIG. 1 is a schematic sectional view of a laser device according to one embodiment of this invention assembled with an endoscope for the medical treatment of a patient's affected coeliac spot.

Description is given with reference to the accompanying drawings of a laser device according to one embodiment of this invention. Referring to FIG. 1, reference numeral 1 denotes a rectangular housing. Provided on the front side of the housing 1 is a light-emitting section 2 formed of a socket for issuing guide beams for illumination and transmission of medical treatment laser beams. The housing 1 contains an infrared laser beam oscillator 3 such as a Nd:YAG-laser and $CO_2$-laser and a nonmonochromic light source 4 formed of, for example, a xenon lamp to issue guide beams or visible beams. A light-guiding optical system 5 is provided between the laser beam oscillator 3 and light source 4 on one hand and the light-emitting section 2 on the other. The optical system 5 comprises a collimator lens 7, laser beam reflector 8 which reflects laser beams but is permeable to guide beams, focusing lens 9 and laser beam reflector 11 which is set on the optical axis 10 of laser beams for their reflection. The laser beam reflector 8 may be formed of, for example, the type which is constructed by vacuum thermal deposition of a dielectric multilayer element on a glass plate. The above-mentioned members are arranged on the optical axis 6 of the guide light beams in the order mentioned. Guide light beams emitted from the light source 4 are rearranged into parallel beams by the collimator lens 7, and pass through the laser reflector 8. Later, the guide beams are focused on the light-emitting section 2 to be drawn out of the housing 1. The laser beam reflector 11 is inclined to the laser beams issued from the light source 3 at an angle of 45° to reflect incoming laser beams at right angles to their traveling direction. The reflected laser beams are carried to another laser beam reflector 8, which is similarly inclined to incoming laser beams at an angle of 45°, thereby causing said incoming laser beams to be transmitted to the light-emitting section 2 at right angles to the direction in which said incoming laser beams were previously sent forth from the laser beam reflector 11. Thus, the optical axis 6 of guide beams issued from the light source 4 and the optical axis 10 of laser beams issued from the laser beam oscillator 3 are aligned beyond the laser beam reflector 8.

Figure 2:
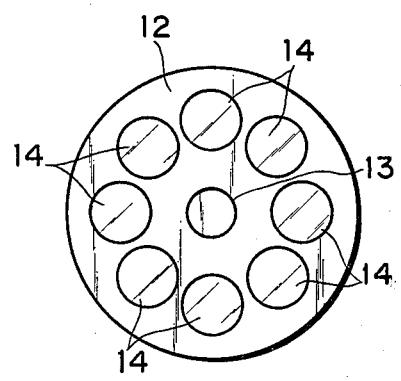

A turntable 12 acting as a color changeover mechanism is set between the collimator lens 7 and laser beam reflector 8. As illustrated in FIG. 2, the turntable 12 is formed of a disc rotatable about a pivotal shaft 13. A plurality of (for example, eight) filters 14 having different colors (one of said filters 14 is transparent to allow for the passage of all white light beams) are mounted on the disc equidistantly in the circumferential direction. The turntable 12 is rotated by a drive device 15, for example, a motor, thereby causing the eight filters 14 to be successively brought to the optical axis of guide light beams. Where a filter 14 having a prescribed color is set on the optical axis of the guide light beams, the turntable 12 ceases to be rotated. At this time, the prescribed filter is made to retain its position by proper means.

A proximal end of a light transmitter or optical fiber bundle 16 is detachably connected to the light emitting section of the housing 1 by means of a connector 17 fitted to said proximal end. The light transmitter 16 withdrawably extends through an insertible section of an endoscope 18. A laser beam-ejecting member 16a provided at the outermost end of the light transmitter 16 is made to properly protrude from the distal end of the endoscope 18. Reference numeral 19 given in FIG. 1 denotes an observation section which is included in a control section set outside of an endoscope body and is intended to observe a patient's coeliac cavity through an observation window formed close to the aforesaid laser beam-ejecting member 16a.

Description is now given of the process of medically treating a patient's affected coeliac spot by applying a laser device arranged as described above.

With the light transmitter 16 is fitted into the endoscope 18. The insertible section of the endoscope 18 is taken to a patient's coeliac cavity. With the laser beam oscillator 3 brought to rest, the light source 4 is actuated. While the inner coeliac wall is illuminated by guide light beams issued from the light source 4, the patient's inner coeliac wall is observed through the observation section 19 to search for an affected spot on the inner coeliac wall. At this time, the turntable 12 is rotated, to let a proper colored fitter 14 be selectively set on the optical axis of guide light beams. This arrangement enables guide light beams to be formed of visible light beams having the same color as, for example, the patient's affected coeliac spot or a color approximately that of said affected spot or visible light beams having a color complementary to the color of said affected spot. Application of the above-mentioned forms of visible guide light beams enables an affected spot of a patient's inner coeliac wall to be observed in sharp distinction from the other wholesome regions of said coeliac wall, thereby making it easy to search for an actually affected spot, and reducing the possiblity of overlooking said affected spot.

After the site of the affected spot has been recognized by the above-mentioned procedure, the laser beam oscillator 3 is actuated to throw laser beams on the affected spot through the laser beam-ejecting member 16a.

In this case, the laser beams and guide light beams are guided by the light-conducting optical system 5 in such a manner that the optical axis 10 of the laser beams and the optical axis 6 of the guide light beams are aligned at the proximal end of the light transmitter 16, thereby enabling both laser beams and guide light beams to be ejected from the same spot. This means that the central part of that region of an object of observation which is illuminated by guide light beams can coincide with that spot of said object of observation on which laser beams are projected, thereby assuring the easy recognition of the spot exposed to laser beams. Where, therefore, a patient's affected coeliac spot is spread over a small area, safe and quick medical treatment by laser beams can be effected. Further, laser beams and guide light beams can be jointly guided by a single light transmitter 16, thereby reducing the diameter of the insertible section of the endoscope 18.

Figure 3:
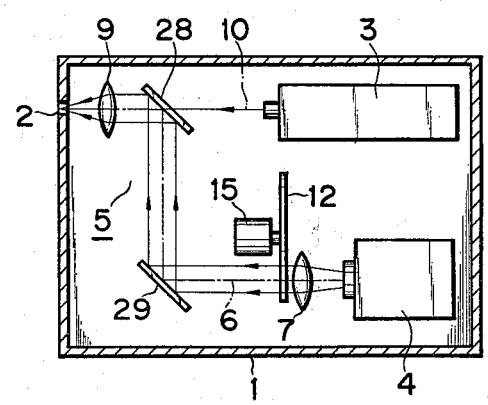

Description is now given with reference to FIGS. 3 to 5 of laser beam devices according to different embodiments of this invention. The parts of FIGS. 3 to 5 the same as those of the first embodiment are denoted by the same numerals, description thereof being omitted.

In the embodiment of FIG. 3, the positions of the laser beam oscillator 3 and light source 4 in the housing 1 are reversed from those shown in FIG. 1. Accordingly, the light-conducting optical system 5 is arranged as described below.

A guide light beam reflector 28 which is permeable to laser beams and reflects all guide light beams, and the focusing lens 9 are set between the light-emitting section 2 and laser beam oscillator 3 on the order mentioned as counted from said laser beam oscillator 3 so as to be positioned on the optical axis of laser beams issued from said laser beam oscillator 3. The collimator lens 7 and turntable 12 are positioned between the guide light beam reflector 29 and light source 4. The guide light beam reflector 29 is inclined to the optical axis 6 of guide light beams at an angle of 45°, thereby reflecting incoming guide light beams toward the aforesaid guide light beam reflector 28. The guide light beam reflector may be formed of, for example, the type which is constructed by thermally depositing a multilayer element unabsorbent of light rays or a quartz plate. Laser beams emitted from the laser beam oscillator 3 and guide light beams issued from the light source 4 are drawn out of the housing 1 through the light-emitting section 2.

With the foregoing embodiments, the laser beam oscillator 3 and light source 4 were so arranged as to cause laser beams and guide light beams to be ejected in parallel with each other. However, this invention need not be limited to this arrangement. But both laser beams and guide light beams may be emitted at any angle relative to each other, by properly changing the arrangement of the light-conducting optical system 5.

Description is now given with reference to FIGS. 4 and 5 of the embodiments in which laser beams and guide light beams are ejected at right angles to each other from the corresponding light sources.

With the embodiment of FIG. 4, the optical axis of laser beams is aligned with the light-emitting section 2. With the embodiment of FIG. 5, the light source 4 is aligned with the light-emitting section 2. With the embodiment of FIG. 4, a guide light beam reflector 28 which is permeable to laser beams emitted from the laser beam oscillator 3 and reflects all guide beams issued from the light source 4 is positioned between the corresponding light sources 3, 4 and the focusing lens 9. With the embodiment of FIG. 5, the laser beam reflector 8 which is permeable to guide beams emitted from the light source 4 and reflects laser beams issued from the laser beam oscillator 3, and conducts both beams to the light-emitting section 2 is positioned between the corresponding light sources and the focusing lens 9.

The embodiments of FIGS. 3 to 5 assure the same effect as the laser device of FIG. 1. Particularly, the embodiments of FIGS. 4 and 5 have the advantage of reducing a number of reflectors by one.

Throughout the foregoing embodiments, guide light beams were made to have an optimum color by applying a plurality of colored filters. However, any arrangement is available, provided it enables guide light beams issued from the light-emitting section 2 to have a proper color.

Description is now given of a modification in this connection with reference to FIG. 6. The laser device of FIG. 6 is formed of a guide light beam source assembled with a target board. A mechanism for emitting guide light beams having the selected colors described with respected to the preceding embodiments comprises a pair of monochromic laser beam oscillators 4a, 4b. A first laser beam oscillator 4a is a helium-neon oscillator, and a second laser beam oscillator 4b is an argon oscillator, and emits blue laser beams. In contrast, the medical treatment laser beam oscillator 3 emits infrared laser beams. Laser beams issued from this medical treatment laser beam oscillator 3 are transmitted along the linear optical axis 10, pass through reflectors 28a, 28b and are focused at the light-emitting section 2 by means of the focusing lens 8. Orange laser beams emitted from the first laser beam oscillator 4a proceed straight forward to one reflector 28a, which reflects the orange laser beams at right angles toward the light-emitting section 2. The reflected orange laser beams are transmitted straight forward along the aforesaid optical axis 10, conducted through the other reflector 28b, focused by the focusing lens 8, sent forth to the light-emitting section 2, and finally drawn out of the housing 1. Blue laser beams issued from the second laser beam oscillator 4b are carried directly to the other reflector 28b, so reflected as to proceed linearly along the optical axis, and finally ejected out of the housing 1 through the light-emitting section 2 as in the ease of the orange laser beams.

The above-mentioned laser beams oscillators 3, 4a, 4b are fitted with the corresponding shutters 30, 31a, 31b whose operation can be externally controlled. Where it is desired to emit a monochromic laser beam, one of the laser beam oscillators 3, 4a, 4b is applied. Where it is desired to issue laser beams having a plurality of colors, any combination of said laser beam oscillators 3, 4a, 4b is used. It is possible to intermittently operate said laser beam oscillators 3, 4a, 4b themselves instead of providing separate shutters.

With the laser device of FIG. 6, guide light beams themselves can be formed of any one selected from the group consisting of orange laser beams sent forth from the first laser beam oscillator 4a, blue laser beams emitted from the second laser beam oscillator 4b, and yellowish white laser beams obtained by a mixture of orange and blue laser beams which results from the simultaneous energization of both laser beam oscillators 4a, 4b.

Therefore, the embodiment of FIG. 6 offers the advantages that an easy search can be made for a patient's affected coeliac spot, and the medical treatment of said affected coeliac spot by projection of infrared laser beams can be effected within that region of the patient's inner coeliac wall which is illuminated by the guide light beams formed of one of the above-listed laser beams, thereby assuring an easy, reliable medical treatment.

With the embodiments of FIG. 6, two laser beam oscillators were used to produce guide light beams. It is possible to apply a larger number of laser beam oscillator in order to produce guide light beams having various colors. Further, the sources of guide light beams used not be limited to those of laser beams. Obviously, it is possible to use any other source of guide light beams, provided it emits visible guide light beams. The guide light sources of the embodiment of FIG. 6 can have their positions varied as in the preceding embodiments.

What is claimed is:

1. A combination of an endoscope and laser device, wherein the endoscope comprises an insertable channel, a laser probe which is detachably taken into the insertable channel and is provided with a light-emitting member projecting from the insertable channel, and an observation section; and the laser device emits medical treatment laser beams and illumination light beams into the endoscope through the laser probe, and comprises a housing provided with a light-emitting section to which the laser probe can be connected, a medical treatment laser beam oscillator held in the housing conprising an infrared laser beam oscillator which can emit laser beams, a light source means received in the housing which can selectively emit at least two visible rays having different colors, said light source means being capable of issuing nonmonochromatic light beam and having means for selectively converting said nonmonochromatic light beams into light beams having at least two different colors comprising two different colored filters and means for selectively setting said two filters on the optical axis of the nonmonochromatic light beams, and an optical system which converges laser beams emitted from the medical treatment laser beam oscillator and visible rays sent forth from the assembly of illumination light sources, thereby conducting said laser beams and illumination light beams to the light-emitting section.

2. The laser device according to claim 1, wherein the medical treatment laser beam oscillator and light source means are set in the housing to cause laser beams and nonmonochromatic light beams to be issued in parallel with each other.

3. The laser device according to claim 1, wherein the medical treatment laser beam oscillator and light source means are arranged to cause laser beams and nonmonochromatic light beams in the directions mutually defining an angle of 90°.

* * * * *